(12) United States Patent
McKay (10) Patent No.: US 9,320,559 B2
(45) Date of Patent: *Apr. 26, 2016

(54) NERVE AND SOFT TISSUE ABLATION DEVICE HAVING RELEASE INSTRUMENT

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/703,199

(22) Filed: May 4, 2015

(65) Prior Publication Data

US 2015/0230850 A1    Aug. 20, 2015

Related U.S. Application Data

(63) Continuation of application No. 13/837,089, filed on Mar. 15, 2013, now Pat. No. 9,023,022.

(51) Int. Cl.
| | |
|---|---|
| *A61B 18/18* | (2006.01) |
| *A61B 18/02* | (2006.01) |
| *A61B 17/00* | (2006.01) |
| *A61B 18/00* | (2006.01) |

(52) U.S. Cl.
CPC ........... *A61B 18/02* (2013.01); *A61B 17/00234* (2013.01); *A61B 18/0218* (2013.01); *A61B 2018/00041* (2013.01); *A61B 2018/00095* (2013.01); *A61B 2018/00166* (2013.01); *A61B 2018/00202* (2013.01); *A61B 2018/00434* (2013.01); *A61B 2018/00565* (2013.01); *A61B 2018/00577* (2013.01); *A61B 2018/0262* (2013.01); *A61B 2018/0293* (2013.01)

(58) Field of Classification Search
CPC ............ A61B 17/00234; A61B 18/02; A61B 18/0218; A61B 2018/00041; A61B 2018/00095; A61B 2018/00166; A61B 2018/00202; A61B 2018/00434; A61B 2018/00565; A61B 2018/00577; A61B 2018/0262; A61B 2018/0293

See application file for complete search history.

(56) References Cited

U.S. PATENT DOCUMENTS

| | | |
|---|---|---|
| 5,147,355 A | 9/1992 | Friedman et al. |
| 5,334,181 A | 8/1994 | Rubinsky et al. |
| 5,520,682 A | 5/1996 | Baust et al. |

(Continued)

FOREIGN PATENT DOCUMENTS

WO    2010102310 A2    9/2010

*Primary Examiner* — George Manuel (74) *Attorney, Agent, or Firm* — Martin & Ferraro LLP (57) ABSTRACT

Ablation devices useful for destroying nerve and soft tissue via a minimally invasive procedure to alleviate pain are provided. The device comprises a probe comprising an interior surface that defines an internal passage and an exterior surface comprising a tip. The internal passage has a filament comprising an opening configured to release a pressurized material into the interior surface of the probe so as to cool the exterior surface of the probe to a selected temperature. A release instrument is provided comprising a sheath that comprises an exterior surface and an interior surface configured for engagement with the probe. The probe tip is configured for ablating nerve and/or soft tissue by forming an ice ball and the release instrument is configured to release the probe tip from the ice ball. Methods for ablating nerve and/or soft tissue utilizing the ablation devices are also provided.

22 Claims, 1 Drawing Sheet

(56) References Cited

U.S. PATENT DOCUMENTS

| | | |
|---|---|---|
| 5,906,612 A | 5/1999 | Chinn |
| 6,032,675 A | 3/2000 | Rubinsky |
| 6,179,831 B1 | 1/2001 | Bliweis |
| 6,190,378 B1 | 2/2001 | Jarvinen |
| 6,485,422 B1 | 11/2002 | Mikus et al. |
| 6,579,287 B2 | 6/2003 | Wittenberger et al. |
| 6,672,095 B1 | 1/2004 | Luo |
| 6,761,715 B2 | 7/2004 | Carroll |
| 6,789,545 B2 | 9/2004 | Littrup et al. |
| 6,796,979 B2 | 9/2004 | Lentz |
| 6,902,547 B2 | 6/2005 | Aves et al. |
| 6,926,711 B2 | 8/2005 | Lentz et al. |
| 7,381,208 B2 | 6/2008 | Van Der Walt et al. |
| 7,510,554 B2 | 3/2009 | Duong et al. |
| 7,625,368 B2 | 12/2009 | Schechter et al. |
| 7,641,679 B2 | 1/2010 | Joye et al. |
| 7,846,154 B2 | 12/2010 | Bliweis et al. |
| 7,938,822 B1 | 5/2011 | Berzak et al. |
| 7,967,814 B2 | 6/2011 | Levin |
| 7,967,815 B1 | 6/2011 | Berzak et al. |
| 8,083,733 B2 | 12/2011 | Toubia et al. |
| 8,162,812 B2 | 4/2012 | Shai et al. |
| 2002/0068964 A1 | 6/2002 | Dobak |
| 2004/0049177 A1 | 3/2004 | Zvuloni et al. |
| 2005/0177215 A1 | 8/2005 | Rosenberg |
| 2005/0240239 A1 | 10/2005 | Boveja et al. |
| 2007/0156125 A1 | 7/2007 | DeLonzor |
| 2007/0191732 A1 | 8/2007 | Voegele |
| 2008/0119839 A1* | 5/2008 | Vancelette ............... 606/23 |
| 2008/0306475 A1 | 12/2008 | Lentz et al. |
| 2009/0036823 A1 | 2/2009 | LePivert |
| 2009/0192505 A1 | 7/2009 | Askew et al. |
| 2009/0299357 A1 | 12/2009 | Zhou |
| 2010/0168739 A1 | 7/2010 | Wu et al. |
| 2010/0179527 A1 | 7/2010 | Watson et al. |
| 2010/0292764 A1 | 11/2010 | Soomro et al. |
| 2011/0270238 A1 | 11/2011 | Rizq et al. |
| 2011/0313411 A1 | 12/2011 | Anderson et al. |
| 2012/0046531 A1 | 2/2012 | Hua |
| 2012/0065630 A1 | 3/2012 | Berzak et al. |
| 2012/0089047 A1 | 4/2012 | Ryba et al. |
| 2012/0109116 A1 | 5/2012 | Asconeguy et al. |
| 2012/0253336 A1 | 10/2012 | Littrup et al. |

\* cited by examiner

NERVE AND SOFT TISSUE ABLATION DEVICE HAVING RELEASE INSTRUMENT

FIELD

The present invention relates, generally to devices and methods for ablating a material or substance. More specifically, the devices and methods are useful for removing nerve and/or soft tissue via a minimally invasive procedure to alleviate pain.

BACKGROUND

Acute and chronic pain management has been a concern for as long as medicine has been practiced. Several methods of inducing analgesia and anesthesia have been developed. For example, the use of chemical, substance's is perhaps the most common approach to pain relief which requires suitable substances that are effective, safe to humans, and do not cause complications or abnormal reactions. Despite the great advances that have been made in the field of anesthesiology, and in the field of pain relief in general, there are still some drawbacks to chemical-based, approaches. For instance, the anesthetics generally available today most be administered in carefully graduated doses to assure the patient's well being, require extended periods of fasting prior to treatment, and are often accompanied by undesirable after effects such as nausea.

One alternative approach that is commonly used for providing pain relief is ablation in which nerves and/or tissue is removed and/or destroyed. Two approaches to removing tissue via ablation are through cold or hot ablation procedures and techniques. Various categories of ablation include but are not limited to electrical, radiation, light, radiofrequency, ultrasound, cryotherapy, thermal, microwave and hydromechanical. One form of hot ablation is radiofrequency ablation. During radiofrequency (RF) ablation, current passing through tissue from the active electrode leads to ion agitation, which is converted by means of friction into heat. The process of cellular heating includes almost immediate and irreparable cellular damage, which, leads to coagulation necrosis. Because ion agitation, and thus tissue heating, is greatest in areas of highest current density (e.g., closest to the active electrode tip), necrosis is limited to a relatively small volume of tissue surrounding the RF electrode.

Another form of ablation uses cold ablation and is called cryoablation. During cryoablation, tissue is frozen or rapid, freeze/thaw cycles are inflicted upon the tissue. There are many advantage's to using cryoablation instead of radiofrequency ablation. For example, cryoablation is safe especially near critical vasculature and there in less risk of post-procedure neuritis or neuromas following neuroablation for the treatment of pain. Cryoablation allows treatment mapping pre and post procedure where areas of tissue can be mapped by limited, reversible and/or freezing. Cryoablation can be monitored and visualized on ultrasonography, CT and MRI. Moreover, because nerve cooling is anesthetic, cryoablation is a less painful procedure than thermal ablation techniques.

The current procedures and techniques using cryoablation used destroy tissue due to rupturing of cells and/or cell organelles within the tissue. Deep tissue freezing is affected by insertion of a tip of a cryosurgical device into the tissue, either transperineally, endoscopically or laparoscopically, and a formation of, what is known in the art as, an ice ball around the tip. During freezing, ice formation within the extracellular space creates an osmotic gradient, resulting in cellular dehydration, ice crystals then form within the cells causing cell membranes to rupture resulting in cell death.

In addition, when the adjacent tissues are present at opposite borders with respect to the freeze treated tissue and since the growth of the ice ball is in a substantially similar rate in all directions toward its periphery, if otherwise, the ice ball reaches one of the borders before it reaches the other border, and decision making must be made on whether to continue the process of freezing, risking damage to close healthy tissues, or to halt the process of freezing, risking a non-complete destruction of the treated tissue.

Traditional cryoablation systems can provide destruction capabilities of soft, tissue via the application of single needles that form an ice ball centered around a tip, but the procedures can take a considerable amount of time to perform because the ice balls are directly attached to the needle tips and a medical practitioner must wait for the ice halls to melt enough in order to remove the needles from the site.

Another problem with currently available cryoablation devices is that they are not cost effective. The needles used during a procedure are disposed of after use and are not reusable.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Accordingly, there is a need for devices and methods to provide efficient destruction of we and/or soft tissue ablation by utilizing a device that allows a medical practitioner to position the components of the device at various locations, such as, for example, multiple facet joints and/or multiple spinal levels such that the medical practitioner can quickly move the device from one location to the next without waiting for an extended, period, of time for ice ball melting to remove the device from the site. Moreover, a device is needed for use during a minimally invasive procedure and/or during an open surgical procedure. Further, there is a need for devices and methods that provide fine ablation capabilities of nerve and/or soft tissue. Devices and methods that assist in the control of necrosis in a tissue being treated are also needed.

SUMMARY

Ablation devices and methods are provided that shorten the length of a procedure and reduce the costs of the procedure. The ablation devices and methods provided allow the tip of the device to the easily separated from an ice ball to obtain more time efficient ablation procedures. In some embodiments, the devices and methods provided are reusable for multiple procedures and are antimicrobial. In some embodiments, the devices and methods provided are not reusable.

In some embodiments, the ablation devices and methods provided, allow destruction of nerves and other soft tissue via a minimally invasive procedure to alleviate pain. The ablation devices and methods disclosed comprise a probe comprising an interior surface defining an Menial passage and an exterior surface comprising a tip. The internal passage has a filament comprising an opening configured to release a pressurised material into the interior surface of the probe so as to cool the exterior surface of the probe to a selected temperature. A release instrument is provided comprising a sheath comprising an exterior surface, and an interior surface configured for engagement with the probe. The probe tip is configured for ablating nerve and/or soft tissue by forming an ice ball and the release instrument is configured to release the probe tip from the ice ball.

In some embodiments, a cryoablation device comprises a probe comprising an interior surface defining an internal passage and an exterior surface comprising a tip. The internal passage has a filament comprising an opening configured to release a pressurized material into the interior surface of the probe so as to cool the exterior surface of the probe to a selected temperature. A release instrument is provided comprising a sheath and a heating element. The tube comprises an exterior surface, and an interior surface configured for engagement with the probe. The probe tip is configured for ablating nerve and/or soft tissue at a painful joint such as, for example, a facet joint sacroiliac joint, or an intervertebral disc by forming an ice ball and the release instrument is configured to release the probe tip from the ice ball.

In certain embodiments, methods for destroying, nerves and other soft tissue via a minimally invasive procedure to alleviate pain are also provided. Destroying the target nerve or soft tissue can eliminate and/or reduce pain symptoms. Specific clinical applications of the disclosed ablation instrument include destruction of nerves causing facet joint, sacroiliac joint, and discogenic back and leg pain, destruction, of soft tissue causing stenosis pain, symptoms, and many other orthopedic and oral maxillofacial pains, ENT pains and pathologies. Ablation will destroy cellular contents, but retain tissue architecture. The destroyed nerve will fill with scar tissue blocking nerve regrowth and conduction.

In some embodiments, a method of ablation is provided. The method comprises: disposing a probe at a surgical site, wherein, the probe comprises an interior surface defining an internal passage and an exterior surface comprising a tip, wherein the internal passage has a filament comprising an opening configured to release a pressurized material into the interior surface of the probe so as to cool the exterior surface of the probe to a selected temperature; placing the probe adjacent to the nerve and/or soft tissue to be ablated so as to form an ice ball; introducing a release instrument comprising a sheath, wherein the sheath comprises an exterior surface, and an interior surface configured for engagement with the probe; and disposing the release instrument about the probe such that the release instrument releases the probe tip from the ice ball.

Additional features and advantages of various embodiments will be set forth in part in the description dial follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard, to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Devices for efficient destruction, and/or removing of a material or substance such as nerve and soft tissue suitable for use in open surgical and/or minimally invasive procedures for the treatment of pain are disclosed. The following description is presented to enable any person skilled in the art to make and use the present disclosure. Descriptions of specific embodiments and applications are provided only as examples and various modifications will be readily apparent to those skilled in the art.

The present disclosure may be understood more readily by reference to the following detailed description of the disclosure presented in connection, with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

DEFINITIONS

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when, values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) mean's rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended, to encompass different orientations of the device in addition to different orientations than those depicted in the figures. Further, terms such as "first", "second", and the like, are also used to describe various elements, regions, sections, etc, and are also not intended to be limiting. Like terms refer to like elements throughout the description.

As used herein, the terms "having", "containing", "including", "comprising" and the like are open ended, terms that indicate the presence of stated elements or features, but do not preclude additional elements or features.

The headings below are not meant to limit the disclosure in any way; embodiments under any one heading may be used in conjunction with embodiments under any other heading.

Reference will now be made in detail to certain embodiments of the invention, examples of which are illustrated, in the accompanying drawings. While the invention will be described in conjunction with the illustrated embodiments, it will be understood that they are not intended to limit the Invention to those embodiments. On the contrary, the invention is intended to cover all alternatives, modifications, and equivalents that may be included within the invention as defined by the appended claims.

Cryoablation

Cryoablation devices have been available to surgeons to treat many medical, conditions, for example, in the treatment of tumors in lung, liver, kidney and other body organs. Cryoablation has also been used for treatment of tumors, cardiac arrhythmias, chronic and post-operative pain, bone fracture and soft tissue wounds.

Cold temperatures have been used to decrease inflammation and to relieve pain since the ancient Egyptians. Liquid air and carbon dioxide were used to treat skin lesions in the beginning of the twentieth century. In 1950, liquid nitrogen was introduced into clinical practice for the cryosurgical ablation of a variety of skin, diseases and allowed for deeper tissue to be treated with cryoablation. In 1961, a liquid nitrogen probe was developed and was used to treat Parkinson's disease as well as inoperable brain tumors. From 1980-2000, systems emerged based on an advanced gas expansion method known as the joule-Thomson Principle. This principle allows for temperature change of a gas or liquid when it is forced through a valve or porous plug while being kept insulated so that no heat is exchanged with the environment. The refrigerant could be stored at room temperature and the difficulties associated with supplying liquid nitrogen to the operating room disappeared. Three main refrigerants were utilized: nitric oxide, liquid nitrogen and argon. For over 20 years, rigid cryoprobes have existed for percutaneous use or in open invasive surgical procedures. For example, cryoprobes are used for freezing a range of lesions from prostate tissue to metastatic cancers in liver. Neuronal tissue has been frozen with such devices for the relief of pain.

Current cryoablation procedures and techniques employ cryoprobes that utilize a needle that forms an ice ball centered around a tip disposed at a surgical site. Before the tip can be positioned into another area of the surgical site, a medical practitioner must wait for the ice ball to adequately melt before removal. Therefore, to ablate multiple areas within the same patient, a considerable amount of time is wasted and the amount of time that it takes to perform a procedure is lengthened. Therefore, the probe of the present disclosure decreases the amount of time wasted dining a surgical, procedure for enhanced ablation.

The present disclosure incorporates a probe and a release instrument into a device that is capable of quickly ablating multiple areas of a surgical, site. The use of a probe and a release instrument in the present disclosure allows a probe to be quickly removed from a surgical site.

Figure 1:
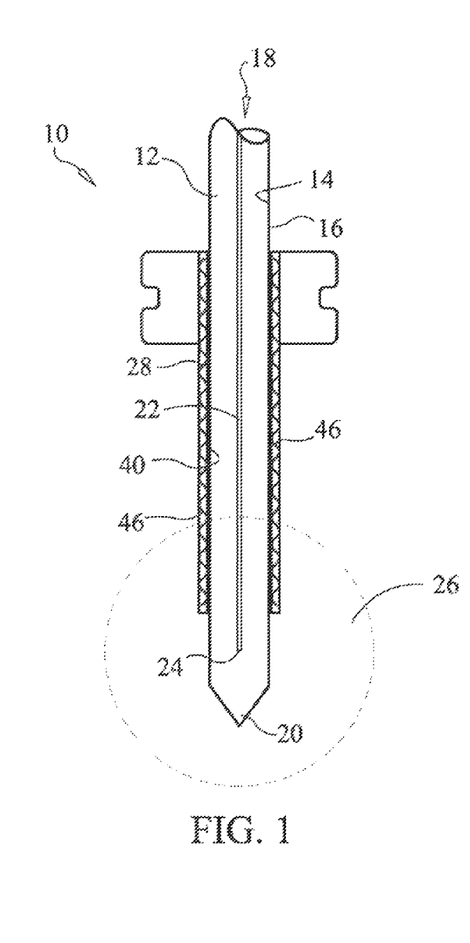
FIG. 1 illustrates a cross sectional view of an ablation device in accordance with one embodiment of the present disclosure.
Figure 2:
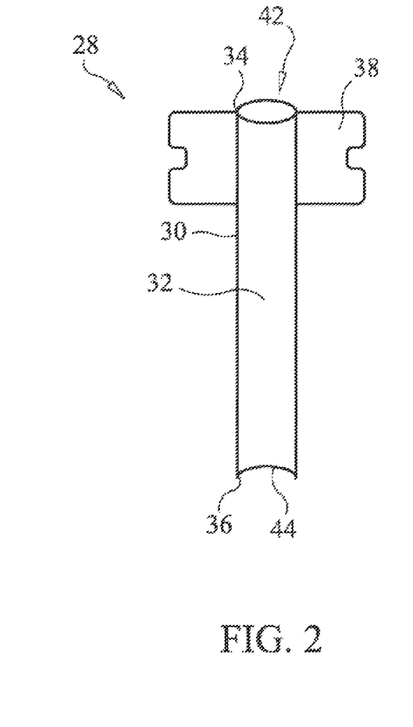
FIG. 2 illustrates, a front view of an ablation device in accordance with one embodiment of the present disclosure.

As illustrated in FIGS. 1-2, the present ablation device 10 comprises a probe 12 (FIG. 1). In various embodiments, device 10 includes a plurality of probes. The dimensions of the device, among other things, will depend on the site that needs ablation. For example, the width of the cervical facet is only about 0.5-1.0 cm and about 1.0-2.0 cm for the lumbar facet region. Thus, the device, in various embodiments, can be designed for these specific areas.

Some examples of lengths of the probe, may include, but are not limited to, from about 50 to 150 mm in length, for example, about 50 mm for the cervical facet use, about 100 mm for a lumbar facet use in a standard adult and about 150 mm for an obese adult patient. The thickness of the probe will depend on the site that needs ablation and/or the particular embodiment of the device. The thickness of the probe is about 20 gauge. In some embodiments, the probe can be about 17 to about 22 gauge, in various embodiments, the thickness includes, but is not limited, to, from about 0.05 to about 1.655. In some embodiments the probe can be increasing and or decreasing in thickness throughout the probe. In some embodiments, the probe may be tapered and/or angled. The probe may be the widest or smallest diameter or a diameter in between for insertion into a human or animal body. In some embodiments, the widest diameter is typically about 14 gauge, while the smallest diameter is about 26 gauge.

Probe 12 includes an interior surface 14 and an exterior surface 16. Interior surface 14 defines an internal passage 18. In some embodiments, probe 12 can have one or more passages defined by the interior surface for a pressurized material to be released into the probe as well as recirculation throughout the probe. Exterior surface 16 comprises a tip 20 positioned at a distal end of the probe. In various embodiments, the exterior surface is rough, smooth, dimpled and/or textured.

In some embodiments, a filament 22 is disposed within the internal passage of the probe. The filament is about 0.016 inches in diameter. In some embodiments, the filament is about 0.010 to 0.015 or about 0.17 to about 0.25 inches in diameter. The filament is a conduit for cooling and expansion of the pressurized material that is released and passed into the probe. The filament, includes an opening 24 configured to release the pressurized material into the interior surface of the probe. The opening may be shaped as a regular or irregular polygon including arcuate, round, square, oblong, kidney shaped, crescent, or beveled shaped. The pressurized material is released and enters into the passage cooling and expanding within the passage via the filament.

The material, is pressurized and in some embodiments, the pressure is from about 3,000 to about 6,000 pounds per square inch (PSI). In various embodiments, the material is in the form of argon, liquid nitrogen, nitric oxide, helium, air, krypton, carbon, dioxide, tetrafluoromethane or xenon. When a high pressure material, such as argon, is used, argon will expand within the interior and form a cryogenic pool at the tip, cooling the surface of the tip. The temperature of the material is coldest at the tip of probe 12. In one embodiment, tip 20 is made of a heat conducting material such as metal so as to enable the formation of an ice ball 26. The ice ball is spherical or oval in shape.

Suitable materials that probe 12 can be made from for example are, polyurethane, polyurea, polyether(amide), PEBA, thermoplastic elastomeric olefin, copolyester, and styrenic thermoplastic elastomer, steel, aluminum, stainless steel titanium, nitinol, tungsten, molybdenum, metal alloys with high non-ferrous metal content and a low relative proportion of iron, carbon fiber, glass fiber, plastics, ceramics or a combination thereof.

In some embodiments, tip 20 is pointed to allow for easy pushing through tissues. In some embodiments, the tip of the probe can be round or tapered. In various embodiments, the tip is smooth for insertion.

In various embodiments, tip 20 can include at least one opening to inject material into a surgical site to facilitate ice ball formation. The openings may be shaped as a regular or irregular polygon including arcuate, round, square, oblong, kidney shaped, crescent, or beveled shaped. In some embodiments, therapeutic agents can be delivered to the surgical site via the at least one opening.

Device 10 includes a release instrument 28 (FIGS. 1-2). In various embodiments, device 10 includes a plurality of release instruments. Some examples of lengths of the release instrument, include, but are not limited to, from about 60 to 200 mm in length, depending on the surgical sire and size of the patient. The thickness of the release instrument will depend on the site that needs ablation and/or the particular embodiment of the device. The thickness of the release instrument is about 20 gauge. In some embodiments, the thickness of the release instrument can be about 16 to about 24 gauge. In various embodiments, the thickness includes, but is not limited to, from about 0.10 to about 1.7. In some embodiments the release instrument can be increasing and or decreasing in thickness throughout the sleeve, in some embodiments, the release instrument may be tapered and/or angled. The release instrument may be the widest or smallest diameter or a diameter in between for insertion into a human or animal body. In some embodiments, the widest diameter is typically about 10 gauge, while the smallest diameter is about 22 gauge. In various embodiments, the diameter can be 10, 12, 14, 16, 18, 20 and/or 22 gauge.

Release instrument 28 comprises a hollow sheath 30. In various embodiments, the sheath is a temperature conductive metal. Examples of various metals include, but are not limited to, stainless steel, titanium, copper, silver, gold, aluminum, brass, platinum, molybdenum and/or tungsten. The sheath comprises an exterior surface 32. The exterior surface is configured for engagement with a patient's tissue and a distal end is configured for engagement with the ice ball, in some embodiments, the exterior surface comprises a depth indicator. The exterior surface defines an opening 34 at a proximal end and an opening 36 at a distal end. In some embodiments, the proximal end of the sheath may include a handle 38. In various embodiments, the handle is configured to be a right handed handle or a left handed handle. The sheath includes an internal surface 40 that defines a passage 42 configured for engagement with the exterior surface of the probe. The sheath translates in an axial, direction relative to the probe to separate the probe tip from the ice ball in some embodiments, the sheath is configured, for slidable engagement with the probe. In some embodiments, the release instrument is attached to a proximal end of probe 12. In various embodiments, the release instrument and probe engage via a friction fit, snap fit, clip, key/keyway clips, threaded engagement and/or male/female engagement. In various embodiments, the release instrument is detachable from probe 12 and can be used with multiple probes. In various embodiments, the sheath covers a portion of the probe. In some embodiments, the sheath covers the entire probe. In some embodiments, the sheath comprises of a lock (not shown) that selectively prevents the release instrument from translating relative to the probe. In various embodiments, the internal surface is rough, smooth, dimpled and/or textured.

In some embodiments, the distal end of the sheath comprises a cutting surface 44. The cutting surface is configured to assist in removing the ice ball from the tip of the probe. In various embodiments, the cutting surface is a blade that can have a regular or irregular polygon shape, such as, for example, a square, a rectangle, a circle, or an oval shape and the shape can comprise a smooth, beveled or ridged edge and/or edges. In some embodiments, the cutting surface can be bifurcated or trifurcated to assist in ice ball removal. In various embodiments, the cutting surface is offset relative to the sheath.

In some embodiments, the release instrument is an insulation sleeve that is pushed down into the ice ball to release the probe from the ice ball when ablation is complete.

In various embodiments, the release instrument comprises a heating element such as, for example, a coil 46. The coil is disposed within the sheath and is configured to warm the sheath so that the release instrument can warm the probe and quickly remove the ice ball from the tip. In some embodiments, the coil assists a patient's body in melting the ice hall. In various embodiments, the coil comprises a metal or other thermal conductor which is energized to emit heat. In some embodiments, the heating element, is an electric coil that can be operated via the use of a controller. In various embodiments, the heating element is disposed, at the distal end of the release instrument. In some embodiments, the beating element is disposed within and/or on discrete portions in and/or on the sheath. In various embodiments, placement of the heating element within and/or on the sheath is offset so as to melt the ice hall directionally. In some embodiments, the heating element is a gas and the sheath comprises chambers where the gas is disposed within. The gas may be pressurized or heated through the use of an electrical source.

In some embodiments, the heating element emits heat such as by convective or conductive heat transfer, by resistive heating due to current flow, or by optical heating with light; a fight emitting element, such as a fiber optic element which transmits light sufficient to melt the ice ball when coupled to a light source. In addition, other elements for melting the ice ball may be suitable.

In some embodiments, a lubricant is provided to assist in the insertion of tip 20 within the nerve and/or soft tissue. In some embodiments, the lubricant can be, without limitation, polyethylene glycol (PEG), hyaluronic acid, hyaluronan, lubricin, polyethylene glycol, and any combinations thereof.

After a period of time, ice ball 26 forms and begins to ablate when the tip of the sleeve is adjacent to nerve and/or soft tissue and when, the temperature at the tip decreases to about −40° C. to about −160° C. The temperature at the surface of the ice ball is 0° C. The temperature declines exponentially towards a cool center where it reaches about −170° C. The ice ball will be formed at about 2 to about 8 minutes alter the material has been released into probe 12. The sphere creates, a zone of complete ablation (about −20° C.) typically located within the ice ball at approximately half way between the center of the ball and its outer surface. In various embodiments, nerve and or soft tissue is completely ablated in about 3 to about 16 minutes. In some embodiments, nerve and or soft tissue is completely ablated in about 3 to about 9 minutes. In some embodiments, the ice ball is not a complete ice ball, for example, a partial or half an ice ball can be formed for complete ablation.

The temperature for cryoablation of the device can be selected by the user and can vary as needed. For example, the temperature that can be selected can be from −180° C., −170° C., −160° C., −150° C., −140° C., −130° C., −120° C., −110° C., −100° C., −50° C., −40° C., −30° C., −20° C., −10° C., −5° C. or to about 0° C. or any temperature in between these numbers.

In some embodiments, a heated material can pass through the internal passage of the probe to heat the pressurized material thereby increasing temperature.

In various embodiments, the device is coated with an antimicrobial coating and/or agents. The antimicrobial coating can include, for example, antibiotics, antifungal antiviral agents or the like. Antimicrobial, agents to treat infection include by way of example and not limitation, antiseptic agents, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Some exemplary antimicrobial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbencillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefoperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxettil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin, hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsome; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin; tromethamine; fumoxicilim; furazolium chloride; furazolium tartrate; fasidate sodium; fusidic acid; ganciclovir and ganciclovir sodium; gentamin sulfate; gloximonam; gramicidin; haloprgin; hetaclilin; hetacillin potassium; hexedine; ibafloxacin; imipenem; isoconazole; isepamcin; isoniazid; josamycin; kanamycin sulfate; kitasamycin; levofurlatadone; levopropylcillin potassium; lexithromycin; lincomycin; lincomycin hydrochloride; lomefloxacin; lomefloxacin hydrochloride; lomefloxacin mesylate; loracarbef; mafenide; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodium; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthirazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetxacycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; ritametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sufamoxole; sulfanilate zinc; sulfanitran; sulfasalazine; sulfasomizole; sulfathiazole; sulfazamet; sulfisoxazole; sulfisoxazole acetyl; selfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In some embodiments, the device can be coated with an antiviral agent. Antiviral, agents can include, but are not limited to, vidarabine, acyclovir, famciclovir, valacyclovir, ganeyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Depending on the particular embodiment, the size of the probe tip determines the size of the ice ball formed. In some embodiments, the length of the tip is about 0.5 to about 2 mm for smaller ice balls and from, about 3 to about 6 mm for larger ice balls.

In various embodiments, the tip of device 10 comprises a telescopic configuration. The tip can be manually or electronically movable so as to place the tip into a particular position within a surgical site. In certain embodiments, all or some of the tip comprise a telescopic configuration. In some embodiments, the tip is a navigational tool, used to guide device 10 into a surgical site.

In some embodiments, the tip and/or sheath of device 10 comprises indicia, for example a depth indicator that may include an analog, such, as, for example, a dial, with a numerical indicator of angle and/or digital display, such as, bar example, LED and/or LCD. The graduations may represent various indicia, such as, for example, numerical, alphabetic and/or specific conditions/orientations, such as, initial depth and/or final depth of penetration into the nerve and/or tissue.

In certain embodiments, device 10 may include switches for manually controlling the operation of device 10 by a medical practitioner. The switches can provide functions such as on/off, cooling, and predetermined cycles of heating and cooling by selectively and controllably communicating device 10 with, an external material container.

In some embodiments, different monitors of temperature, gas pressure and location on device 10 can be attached to device 10, in some embodiments, thermal, sensors may be used for measuring the temperature of the material, the tip and/or the release instrument. In some embodiments, device 10 can be operative connected to semi-steerable or navigational sources for easier guidance into tissues. In various embodiments, the navigational sources can be coupled with a pre-procedure such as for example, CT, MRI, PET scan, etc, so that the target nerve or soft tissue to be ablated can be identified and accurately located during the procedure.

In some embodiments, device 10 is attached to a pressure source that is configured to supply the pressurized material described above. In some embodiments, without limitation, the pressure source can be a pump, a cannula and or a catheter.

In various embodiment, at a proximal end, device 10 can be operatively connected to a vacuum (not shown) for providing suction to ablated, nerve and/or tissue. The vacuum, may be used to transmit vacuum from a vacuum, source (not shown) to a receiving aperture (not shown) connected to device 10. Any suitable aspirator, cylindrical or otherwise, or other mechanism that creates vacuum upon the movement of an actuating member thereof, may be utilized as a vacuum source. The vacuum can be in communication with the tip of device 10 for providing suction to remove ablated nerve and/or soft, tissue.

With, further reference to FIGS. 1-2, not shown, is an overall glass or other insulating layer covering most of the structure, in some embodiments, the coating or insulating layer can be glass or ceramic having a thickness from about 0.005 to about 0.5 mm thick or from about 0.01 to about 0.2 mm thick.

The glass type insulation is typically applied by a conventional process of dipping each relevant component prior to assembly in liquid (molten) glass and then annealing the glass. In some embodiments, the coating or insulation layer does not cover the entire probe. In some embodiments, the coating or insulation layer does cover the entire probe.

In various embodiments, the device may include radiographic markers to help indicate position on Imaging procedures (e.g., CT scan, X-ray, fluoroscopy, PET scan, etc.). These may be disposed on or a portion of the device and include, but are not limited to, barium, calcium phosphate, and/or metal beads.

In some embodiments, device 10 can also have a blunt release instrument and/or a probe tip. As a result, the surgeon or health practitioner can eliminate any difficulty in positioning the tips in the optimal location to get an optimal and consistent clinical result. The use of device 10 also results in avoiding necrosis of adjacent tissue, which can lead to clinical adverse events and requires these adjacent tissues to have to repair themselves. Positioning of the tip allows cryoablation to be applied near the tip and avoids hemisphere spacing around the tip to avoid unwanted necrosis.

In some embodiments, the release instrument and/or probe tips can comprise grooves (not shown). Grooves can have edges shaped as a regular or irregular polygon including arcuate, round, square, oblong, oval, kidney shaped, beveled, or crescent shaped. The grooves can also include ridges or have no ridges. In various embodiments, the grooves are located at the tip and can be closed, when device 10 is inactive as device 10 is inserted towards the desired location. Once the nerve or soft tissue to resect, is reached, grooves open, the material becomes activated to ablate the nerve or tissue protruding into each groove as device 10 is manually pushed into it.

In certain, embodiments, device 10 can be provided with a tube or small channel (not shown) configured, to deliver at the location of the severed nerve and/or soft tissue cement or polymer which can provide a physical barrier to prevent the temporary or permanent re-growth of nerve and/or soft tissue so that the pain symptoms do not return. This channel can be adjacent to the internal passage of the release instrument and can run parallel to the passage such that the device can ablate and deliver a therapeutic material or barrier (e.g., polymer, cement, gel, etc.) to the area after ablating it.

Methods for Ablation

The present disclosure also provides methods for destroying or removing nerve and/or soft tissue. The methods comprise disposing a probe at a surgical, site, wherein the probe comprises an interior surface defining an internal passage and an exterior surface comprising a tip, wherein the internal passage has a filament comprising an opening configured to release a pressurized material into the interior surface of the probe so as to cool the exterior surface of the probe to a selected temperature; placing the probe adjacent to a nerve and/or soft tissue such as, for example, a facet joint or sacroiliac joint to ablate the nerve and/or soft tissue by forming an ice ball; introducing a release instrument comprising a sheath, wherein the sheath comprises an exterior surface, and an interior surface configured for engagement with the probe; and translating the release instrument axially about the probe such that the release instrument releases the probe tip from the ice ball.

In various embodiments, the ice ball, forms at about 2-8 minutes and the nerve is ablated in about 3 to 16 minutes. In some embodiments, the release instrument comprises a proximal end comprising a handle and a distal end comprising a cutting surface. In various embodiments, the release instrument comprises a heating element configured to warm the release element such that the release of the ice ball from the probe tip is shortened. In some embodiments, the interior surface of the sheath, translates in an axial direction relative to the exterior surface of the probe and a distal end of the release instrument comprises a cutting surface that engages with the ice ball to separate the ice ball from, the probe tip.

In other embodiments, the methods of the present disclosure further include delivering cement and/or a polymer through a small channel, for injection at the site of the nerve and/or soft tissue destruction, to provide a physically barrier at the location of the nerve destruction, to prevent temporary or permanent nerve regrowth, repair and return of the pain, symptoms.

The barrier material utilized can be any suitable material effective to prevent or at least substantially inhibit the migration of substances that regrow tissue. Illustratively the barrier material can comprise a biodegradable synthetic polymer, in either flowable (and potentially hardenable) or non-flowable form. Illustratively, preferred banter materials can have a first relatively flowable state during delivery and a second relatively less flowable state after implantation. For example, the barrier material may remain in an uncured, deformable, or otherwise configurable state during introduction, and rapidly cure, become harder or solidify after being introduced. Suitable materials that, may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. In some embodiments, the barrier material can be a cement.

In several embodiments, the methods disclosed herein include operatively coupling the device to a source of navigational capability to allow easier pushing through the tissues. In various embodiments, the methods of ablation disclosed herein can include a pre-procedure step wherein the device can be coupled to a CT or MRI machine so that the target nerve and/or soft tissue to be ablated can be identified, and accurately located during the destruction procedure.

The methods for ablation described hereinabove allow complete destruction of the nerve avoiding the problems and partial effectiveness of current cryoablation and RF devices available in the art, and also allow for more complete destruction of soft tissue that is causing stenosis pain symptoms.

In various embodiments, kits are provided that include device 10. The kits can include at least one probe and at least one release instrument. In some embodiments, the probe and/or the release instrument is made reusable for multiple procedures after cleaning and sterilization.

Specific clinical, application of this instrument include destruction of nerves causing facet and discogenic back, and leg pain, destruction of soft tissue causing stenosis pain symptoms, and many other orthopedic and oral maxillofacial pain. Many other painful conditions, associated with arthroscopic, otolaryngological or spinal, procedures could use the ablation devices and methods of using these ablation devices described herein.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An ablation device comprising:
   a probe, the probe defining an axis and comprising an interior surface, the interior surface defining at least one internal passage, and an exterior surface, the exterior surface comprising a probe tip, wherein the at least one internal passage includes a filament, the filament being configured to release a pressurized material into the interior surface of the probe to cool the exterior surface of the probe to a selected temperature, the selected temperature forming an ice ball at the probe tip, the ice ball being adapted to ablate one of nerve and soft tissue, and wherein the at least one internal passage is configured to recirculate the pressurized material through the probe; and
   a release instrument, the release instrument comprising a sheath, the sheath including an exterior surface, a proximal end, a distal end, the distal end including a distal edge, and an interior surface, the interior surface of the sheath being configured for engagement with at least a portion of the outer surface of the probe, the distal edge of the release instrument being configured to release the ice ball from the probe tip.

2. An ablation device of claim 1, wherein the nerve and/or soft tissue comprises one of a facet and a sacroiliac joint.

3. An ablation device of claim 1, wherein the pressurized material comprises one of a liquid and a gas, the one of the liquid and the gas comprising at least one of argon, liquid nitrogen, nitric oxide, helium, air, krypton, carbon dioxide, tetrafluoromethane and xenon, wherein the temperature of the pressurized material decreases at least proximate the probe tip, wherein the pressurized material is cooled at the probe tip to approximately −100° C. through −180° C. wherein the ice ball forms in about 2-8 minutes after the pressurized material is released, and wherein the one of the nerve and soft tissue is ablated in about 3 to 16 minutes after application of the ice ball to the one of the nerve and soft tissue.

4. An ablation device of claim 1, further comprising a heating element disposed within the sheath.

5. An ablation device of claim 1, wherein the proximal end of the release element comprises a handle and the distal edge of the release element comprises a cutting surface.

6. An ablation device of claim 5, wherein the cutting surface comprises a cutting blade.

7. An ablation device of claim 6, wherein the cutting blade comprises one of a regular and an irregular polygon shape, the one of a regular and an irregular polygon shape comprising one of a square, a rectangle, a circle, and an oval shape, wherein the shape further comprises one of a smooth edge, a beveled edge and a ridged edge.

8. An ablation device of claim 1, wherein the sheath of the release instrument comprises a hollow sheath, the hollow sheath having a thickness, the thickness being about 18 gauge.

9. An ablation device of claim 1, wherein the release instrument comprises a metal, the metal comprising one of stainless steel, copper, silver, gold, aluminum, brass, platinum, molybdenum, tungsten, titanium, metal alloys thereof, and a combination thereof.

10. An ablation device of claim 1, wherein the filament comprises an opening, the opening being configured to release the pressurized material into the interior surface of the probe.

11. An ablation device comprising:
a probe comprising an interior surface defining at least one internal passage, and an exterior surface comprising a tip, wherein the at least one internal passage includes a filament, the filament comprising an opening configured to release a pressurized material into the interior surface of the probe to cool the exterior surface of the probe to a selected temperature, and wherein the at least one internal passage is configured to recirculate the pressurized material through the probe, and
a release instrument comprising a sheath, wherein the sheath comprises an exterior surface and an interior surface, the interior surface configured for engagement with the probe, wherein the probe tip is configured for ablating one of nerve and soft tissue by forming an ice ball; and
wherein the release instrument translates in an axial direction relative to the probe to separate the probe tip from the ice ball.

12. An ablation device comprising:
a probe comprising an interior surface defining at least one internal passage, and an exterior surface comprising a tip, wherein the at least one internal passage includes a filament, the filament comprising an open configured to release a pressurized material into the interior surface of the probe so as to cool the exterior surface of the probe to a selected temperature, and wherein the at least one internal passage is configured to recirculate the pressurized material through the probe, and
a release instrument comprising a sheath, wherein the sheath comprises an exterior surface and an interior surface, the interior surface configured for engagement with the probe, wherein the probe tip is configured for ablating one of nerve and soft tissue by forming an ice ball; and
wherein the interior surface of the release instrument is configured for slidable engagement with the exterior surface of the probe.

13. A cryoablation device comprising:
a probe comprising an interior surface defining at least one internal passage, and an exterior surface comprising a tip, wherein the at least one internal passage includes a filament, the filament comprising an opening configured to release a pressurized material into the interior surface of the probe to cool the exterior surface of the probe to a selected temperature, wherein the at least one internal passage is further configured to recirculate the pressurized material through the probe; and
a release instrument comprising a sheath, wherein the sheath comprises an exterior surface, and an interior surface configured for engagement with the probe, wherein the probe is configured for ablating one of nerve and soft tissue by forming an ice ball, and the release instrument is configured to release the ice ball from the probe tip.

14. A cryoablation device of claim 13, wherein the probe is about a 20 gauge needle having one of a pointed tip and a blunt tip, wherein the probe comprises one of titanium, stainless steel, tungsten, molybdenum and alloys thereof, and the pressurized material comprises one of a liquid and a gas, the one of a liquid and a gas comprising one of argon, liquid nitrogen, nitric oxide, helium, air, krypton, carbon dioxide, tetrafluoromethane and xenon, wherein the temperature of the pressurized material decreases at or near the tip, and wherein the pressurized material is cooled at the tip to approximately −100° C. to approximately −180°, and the ice ball forms in about 2-8 minutes after the pressurized material is released, and wherein the nerve is ablated in about 3-16 minutes after application of the ice ball to the one of the nerve and the soft tissue.

15. A cryoablation device of claim 13, wherein the release instrument further comprises a heating element the heating element having a coil, the coil being configured for applying heat to the sheath, the heat adapted to reduce a length of time required to release the ice ball from the probe tip.

16. A cryoablation device of claim 13, wherein the interior surface of the sheath translates in an axial direction relative to the exterior surface of the probe to release the ice ball from the probe tip.

17. A cryoablation device of claim 13, wherein the release instrument comprises a proximal end comprising a handle and a distal end comprising a cutting surface.

18. A cryoablation device of claim 13, wherein the release instrument comprises a metal, the metal comprising at least one of copper, silver, gold, aluminum, brass, platinum, molybdenum and tungsten, wherein the release instrument further comprises a hollow sheath, the hollow sheath having a thickness, the thickness being about 18 gauge.

19. A method of ablating at least one of nerve and soft tissue, the method comprising:
inserting an ablation device the ablation device comprising:
a probe, the probe defining an axis, and comprising an interior surface the interior surface defining at least one internal passage, and an exterior surface, the exterior surface comprising a probe tip, wherein the at least one internal passage includes a filament, the filament being configured to release a pressurized material into the interior surface of the robe to cool the exterior surface of the probe to a selected temperature, the selected temperature forming an ice ball at the probe tip, wherein the ice ball is adapted to ablate one of nerve and soft tissue, and wherein the at least one internal passage is configured to recirculate the pressurized material through the probe; and
a release instrument, the release instrument comprising a sheath, the sheath including an exterior surface, a proximal end, a distal end, the distal end including a distal edge, and an interior surface, the interior surface being configured for engagement with at least a portion of the outer surface of the probe, the distal edge of the release instrument being configured to release the ice ball from the probe tip;
placing at least the ice ball adjacent to the one of the nerve and the soft tissue, thereby ablating the one of the nerve and the soft tissue; and
moving the release instrument, axially about the probe, wherein the release instrument releases the ice ball from the probe tip.

20. A method of claim 19, wherein, the ice ball forms in about 2-8 minutes after the pressurized material is released and wherein the one of the nerve and the soft tissue is ablated in about 3 to 16 minutes after application of the ice ball thereto.

21. A method of claim 19, wherein the release instrument comprises a proximal end comprising a handle and a distal end comprising a cutting surface.

22. A method of claim 19, wherein the interior surface of the sheath translates in an axial direction relative to the exterior surface of the probe and a distal end of the release instrument comprises a cutting surface that engages with the ice ball to separate the ice ball from the probe tip.

* * * * *